(12) United States Patent
Sias

(10) Patent No.: US 7,611,458 B2
(45) Date of Patent: Nov. 3, 2009

(54) ROTATING OPERATING ANOSCOPE

(76) Inventor: Francesco Sias, C. so Villario Emmanuela, 300, Cagliari (IT) I-09131

(\*) Notice: Subject to any disclaimer, the term of this patent is extended or adjusted under 35 U.S.C. 154(b) by 489 days.

(21) Appl. No.: 10/527,133

(22) PCT Filed: Sep. 5, 2003

(86) PCT No.: PCT/IB03/03781

§ 371 (c)(1),
(2), (4) Date: Mar. 8, 2005

(87) PCT Pub. No.: WO2004/021874

PCT Pub. Date: Mar. 18, 2004

(65) Prior Publication Data

US 2006/0036129 A1    Feb. 16, 2006

(30) Foreign Application Priority Data

Sep. 9, 2002   (IT) .................... MO2002A0246

(51) Int. Cl.
  *A61B 1/00*  (2006.01)
(52) U.S. Cl. .................. 600/136; 600/114; 600/130; 600/184
(58) Field of Classification Search ............. 600/184, 600/190, 200, 208, 210, 217, 219, 221, 224, 600/114, 130, 140, 147, 196
See application file for complete search history.

(56) References Cited

U.S. PATENT DOCUMENTS

| 348,843 | A | * | 9/1886 | Hamilton | 600/184 |
|---|---|---|---|---|---|
| 2,482,971 | A | * | 9/1949 | Golson | 600/184 |
| 4,538,594 | A | * | 9/1985 | Boebel et al. | 600/102 |
| 4,834,067 | A | * | 5/1989 | Block | 600/184 |
| 5,345,926 | A | * | 9/1994 | Chikama | 600/200 |
| 5,464,412 | A | | 11/1995 | Budding | |
| 5,507,717 | A | * | 4/1996 | Kura et al. | 600/146 |
| 6,126,594 | A | | 10/2000 | Bayer | |
| 6,142,931 | A | * | 11/2000 | Kaji | 600/114 |
| 6,142,933 | A | * | 11/2000 | Longo et al. | 600/184 |

FOREIGN PATENT DOCUMENTS

WO  01/43626 A1  6/2001

OTHER PUBLICATIONS

International Search Report PCT/IB03/03781, Dec. 10, 2003.

\* cited by examiner

*Primary Examiner*—Linda C Dvorak
*Assistant Examiner*—Alireza Nia
(74) *Attorney, Agent, or Firm*—Nixon & Vanderhye P.C.

(57) ABSTRACT

An anoscope includes a first hollow body open at opposite ends and a second hollow body open at opposite ends shapingly coupled with the first hollow body and arranged to coaxially rotate inside the first hollow body, the second hollow body being provided with a window arranged to make a portion of rectal mucous accessible. The window has an operating window and has dimensions and a shape such as to enable a surgical device to intervene on the portion. An angular positioning element is arranged to regulate the angular position of the second hollow body in the first hollow body in preset reciprocal angular positions, which reciprocal angular positions correspond to a same number of positions that can be taken up by the window.

16 Claims, 3 Drawing Sheets

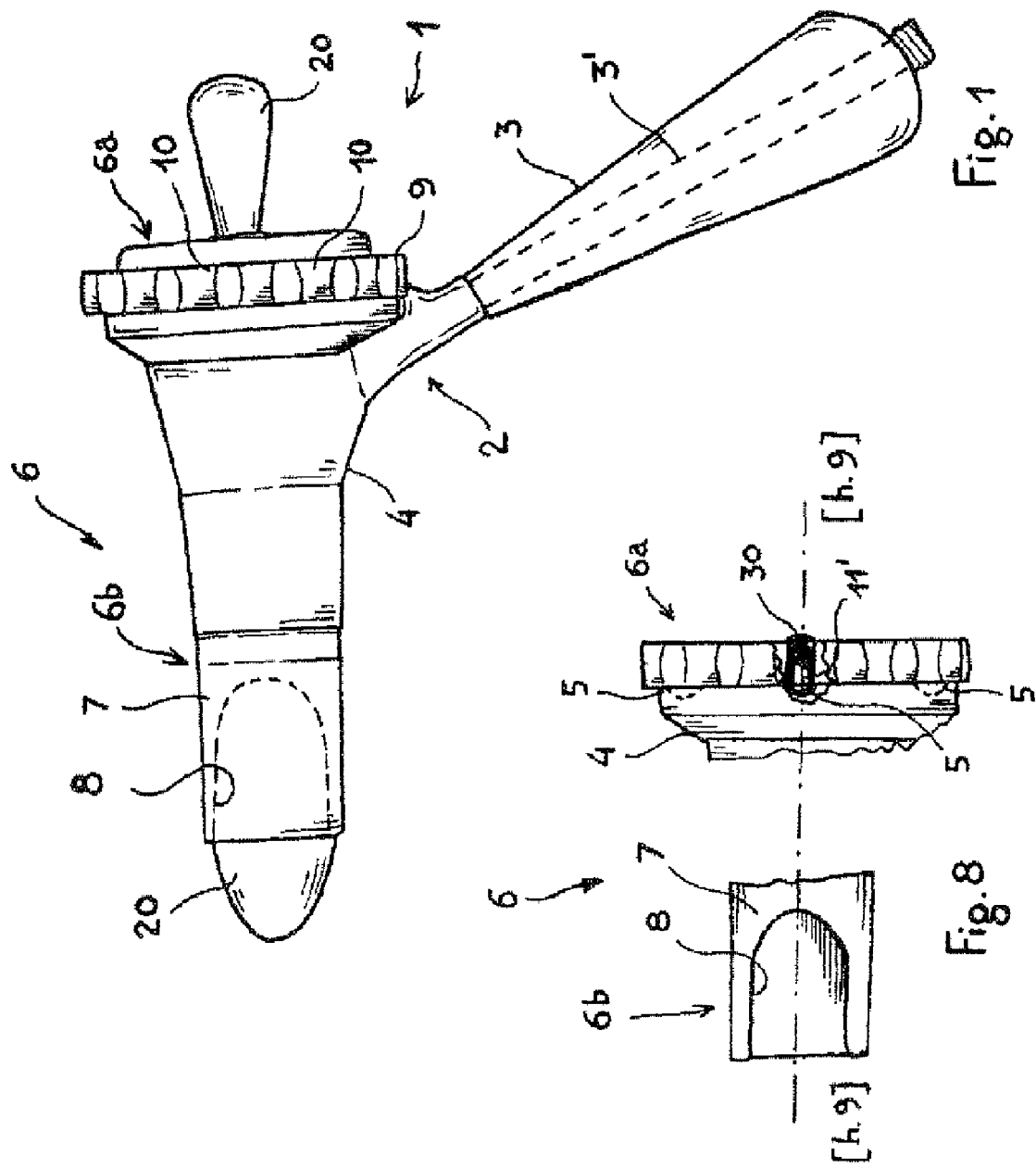

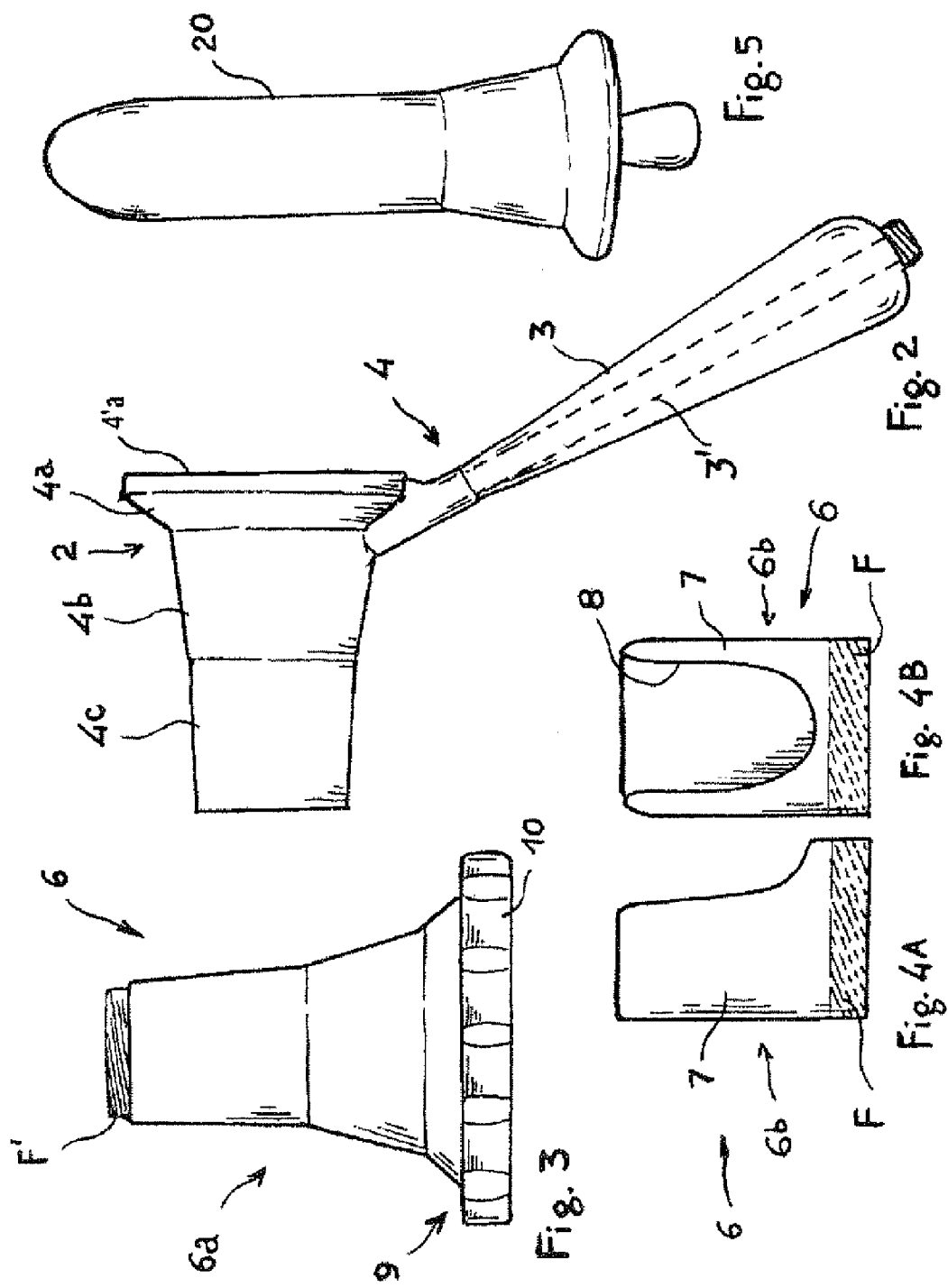

ROTATING OPERATING ANOSCOPE

This application is the US national phase of international application PCT/IB 2003/003781 filed 5 Sep. 2003, which designated the U.S. and claims benefit of IT M02002A000246, dated 9 September 2002,the entire contents of each of which are hereby incorporated by reference.

The present invention concerns an anoscope that can be used in proctology as a diagnostic and/or surgical instrument, said anoscope being provided with a guided-rotation device that is particularly useful for carrying out surgical treatment of haemorrhoids.

Anoscopes are prior-art instruments that are used in general medicine, gastroenterology, proctology, endoscopy and general surgery.

A generic anoscope usually comprises a portion called "speculum", having a cylindrical or tapered-cylindrical shape, that can be handled by an operator by a grip and that is arranged to be inserted through the anus into the terminal segment of the rectum of a patient. The speculum is hollow, open at opposite ends, and is inserted together with a dilator that has a cylindrical shape with a rounded end and which is provided with a smooth surface, and is furthermore substantially longer than the speculum. The dilator is accommodated inside the speculum during the insertion manoeuvre and acts by distending the muscular wall of the rectum without harming the mucous membrane thereof. Once the maneuver has been completed the dilator is extracted whilst the speculum remains in place.

In this way temporary dilatation that is restricted to the terminal segment of the intestinal lumen is obtained, and such dilatation can be used to easily insert further instruments and thus carry out diagnostic and/or surgical operations.

One of the methods for surgically treating hemorrhoids involves obliterating the arterial branches that are afferent to them, i.e. binding through suturing the walls of these vessels in such a way as to form a constriction that interrupts the blood flow towards the haemorrhoids.

For this purpose anoscopes are used wherein the above-mentioned speculum has a cut on its side wall in such a way as to create an 'operating window' through which surgical instruments (forceps, suture needle holders) come into contact with the intestinal mucous membrane in proximity to the operating site, taking advantage of the fact that the mucous membrane protrudes inside the speculum at the above-mentioned window.

One disadvantage of said anoscopes consists of the fact that the operating window opens on a set area of the speculum. If, as generally happens, a surgeon has to treat several hemorrhoids in a same patient during a single operation, the speculum must be rotated so as to reposition the window near the arterial branch concerned. To carry out this maneuver, it is necessary to first insert the previously described dilator to distend the rectal mucous membrane at the operating window and thereby prevent the mucous membrane being 'pinched' in the window during shifting of the latter. The speculum is then gripped and it is rotated around its longitudinal axis according to a rotation angle that is such as to place the window in the desired position.

Obviously, such manoeuvres lengthen the duration of the operation for the surgeon and therefore subject the patient undergoing the surgery to greater distress.

U.S. Pat. No. 6,126,594 discloses an anoscope that can be used to treat hemorrhoids and which is characterized by the presence of a plurality of openings arranged parallel to one another in the body of the speculum, in such a way as to provide a surgeon with a multiplicity of operating windows that can be used simultaneously. In practice, such device has the disadvantage that the rectal mucous membrane may simultaneously protrude into a plurality of zones, thereby obstructing the internal cavity of the speculum, i.e. the field of operation itself. Anoscopes have also been created (see for example the "Welch Allyn" model 38850/38900), wherein the speculum is movable, being hinged on a fixed portion and therefore being rotatable around its own longitudinal axis. Such anoscopes are, however, made for merely diagnostic purposes, i.e. in order to enable a 360° view of the lumen of the rectum and are provided with a window that extends over the entire length of the part of the body of the speculum that is inserted (i.e. that portion of speculum that is actually inserted into the rectal canal).

This technical expedient is certainly useful for exploring the terminal segment of the intestinal cavity without neglecting any area of the mucous membrane, but which causes a massive protrusion of the mucous membrane itself within the speculum that is due to the dimensions of the window. As has already been said, a such phenomenon is disadvantageous during a surgical operation because it causes undesired visual and material obstruction of the operating area.

Furthermore, new surgical techniques are becoming widespread for performing which the prior-art instruments are not always suitable. For example, Dr Francesco Sias (Santa Rita Clinic, Cagliari) recently perfected a method (haemorrhoidal dearterialization with transanal anopexy) that enables hemorrhoids to be treated surgically in a day hospital, that can be carried out without anaesthesia. Such method is based on an anatomical feature, i.e. on the constant presence (documented by Doppler echography) of 6 terminal arterial branches coming from the lower haemorrhoidal artery, said arterial branches being arranged along the wall of the rectum according to a precise geometry and at the end of which the hemorrhoids appear.

In fact, by arranging a patient in a prone position, so as to have the anal opening arranged frontally, the above-mentioned 6 arterial branches are placed on an imaginary clock-face at 1 o'clock, at 3 o'clock, at 5 o'clock, at 7 o'clock, at 9 o'clock, at 11 o'clock. The surgeon may thus make a ligature of said arterial branches (through a so-called "Z" suture) by intervening above the haemorroids. Furthermore, the region of mucous membrane of the rectum subjected to the operation is substantially devoid of sensitive nerves, thus making local anaesthesia unnecessary. Such an operation enables operating time to be halved compared with other types of surgical treatment of hemorrhoids and does not require the patient to be admitted as an inpatient.

However, this method requires a plurality of sutures to be carried out in preset positions.

It is obvious that none of the anoscopes disclosed up until now is ideal for the application of the method. In fact, by using an anoscope with a single window the instrument has to be rotated six times during the operation, with the disadvantages illustrated previously. It would be similarly disadvantageous to use an anoscope with multiple windows or a rotating anoscope, because in both cases the intestinal mucous membrane would take up an undesirable amount of space in the field of operation.

In addition, it should be added that none of the above-mentioned instruments is provided with devices that help the surgeon to position the operating window exactly at the arterial branch that is to be sutured.

An aim of the present invention is to improve the anoscopes that can be used in operating practice.

A further aim is to provide an anoscope equipped with operating windows that can be positioned near the arterial branches to be treated without having to rotate the entire instrument.

Another aim is to provide operating windows of dimensions such as to make accessible only the portions of rectal mucous membrane that are actually concerned by the surgical treatment.

Another further aim is to provide an anoscope that is more compact, which is useful during transport and/or storage.

Yet another further aim is to provide an anoscope that enables an operating window to be rapidly and exactly positioned during the performance of a method for treating haemorrhoids involving suturing arterial branches located in known positions in relation to the axis of the rectum.

In a first aspect of the invention an anoscope is provided, comprising a first hollow body open at opposite ends and a second hollow body open at opposite ends shapingly coupled with said first hollow body and arranged to coaxially rotate inside said first hollow body, said second hollow body being provided with a window arranged to make a portion of rectal mucous membrane accessible, wherein said window has dimensions and a shape such as to enable a surgical device to intervene on said portion.

An anoscope conceived in this manner enables an operating window to be subsequently positioned at different points of the rectal mucous membrane by acting simply on a part of the anoscope and without having to rotate the entire instrument.

The operating window is of dimensions such as to ensure access only to the areas of the rectal mucous membrane that are actually concerned by the treatment, thereby avoiding the protrusion into the hollow body of excessive portions of mucous membrane, with consequent take-up of space in the field of operation.

Also, the first hollow body comprises a grip that facilitates the insertion of the anoscope in the rectal canal and can accommodate a light-beam device to enable illumination of the field of operating.

In a further embodiment, the second hollow body may comprise two separate segments that can be associated to each other before use in such a way as to be able to reduce the dimensions of the anoscope during transport and storage.

In a second aspect of the invention an anoscope is provided, comprising a first hollow body open at opposite ends and a second hollow body open at opposite ends shapingly coupled with said first hollow body and arranged to coaxially rotate inside said first hollow body, said second hollow body being provided with a window arranged to make a portion of rectal mucous membrane accessible, wherein an angular positioning element is furthermore provided arranged to adjust the relative angular position of said second hollow body in said first hollow body in preset reciprocal angular positions.

In an embodiment, said angular positioning element comprises an adjusting ring nut that controls 360° rotation of said second hollow body, enabling the latter to be locked in six alternative positions, corresponding to the same number of positions taken up by the operating window in relation to the internal rectum wall. Said positions are the same as the ones indicated by the Sias method for surgical treatment of haemorrhoids disclosed above.

In order that the invention may be clearly and completely disclosed, reference will now be made, by way of examples that do not limit the scope of the invention, to the accompanying drawings, wherein FIG. 1 shows a rotating operating anoscope complete with dilator;

FIGS. 2 to 7a show the individual elements making up the anoscope in FIG. 1, namely:

FIG. 2 is a side view of the fixed portion of the anoscope, complete with a grip for the operator;

FIG. 3 is a side view of the segment of movable portion of the anoscope not comprising the operating window;

FIGS. 4A and 4B are two different side views of the segment of movable portion of the anoscope comprising the operating window;

FIG. 5 is a side view of the dilator contained in the anoscope in FIG. 1;

FIG. 6 is an incomplete front view of the fixed portion shown in FIG. 2;

FIG. 7 is a front view of the segment of movable portion shown in FIG. 3;

FIG. 7A is an enlarged detail illustrating a device comprised in the segment of movable portion shown in FIG. 7.

FIG. 8 is an interrupted side view of the anoscope, showing the positioning mechanism of the operating window.

Figure 7:
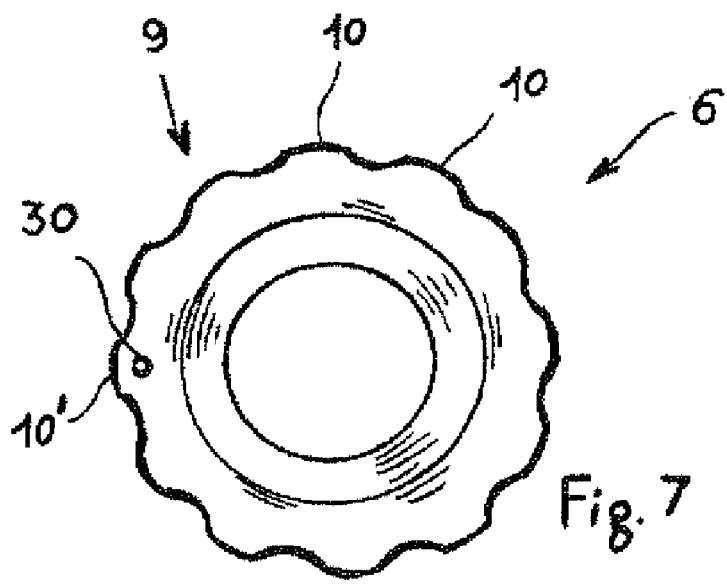
Figure 7A:
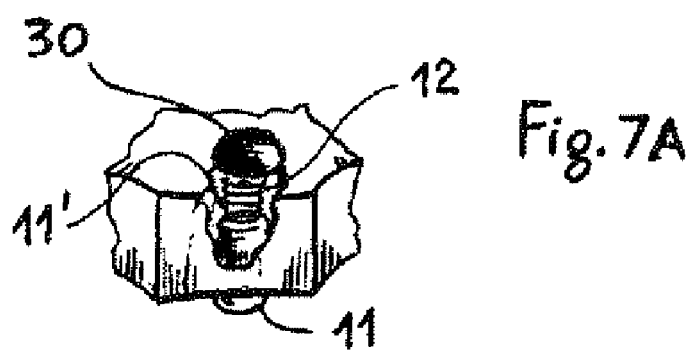

With reference to FIGS. 1 and 2, a rotating operating anoscope 1 comprises a fixed portion 2, comprising in turn a grip 3 that is joined to a support element 4, made of a material that can be sterilised, for example steel, and arranged to penetrate the rectal canal through the anal orifice. The grip 3 internally comprises a coaxial optic guide 3' (indicated by a broken line) arranged to accommodate a light-beam device (not indicated) that can be used to illuminate the field of operation, i.e. the internal cavity of the anoscope 1.

The support element 4 comprises a first truncated-cone portion 4a, a second truncated-cone portion 4b and a third truncated-cone portion 4c, that are joined together and internally hollow. The above-mentioned truncated-cone portions have diameters that decrease from the first truncated-cone portion 4 to the third truncated-cone portion 4c, so that the end of the support element 4 comprising the base of the truncated-cone portion 4a has a diameter that is noticeably greater than the diameter of the end opposite the support element 4, comprising the truncated-cone portion 4c.

Figure 6:
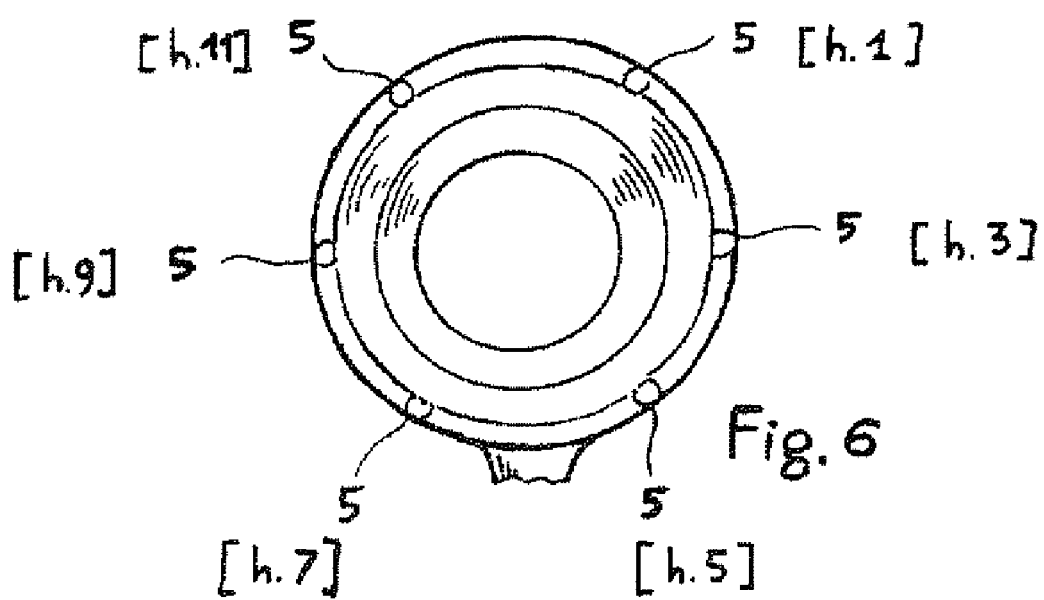

With reference to FIG. 6, the above-mentioned base of the truncated-cone portion 4a, which corresponds to the end of the anoscope 1 facing the operator during use, comprises an edge 4'a that houses a plurality of notches 5. More exactly, there are 6 notches arranged at regular intervals along the edge 4'a. By making the edge 4'a coincide with the circular perimeter of an imaginary clock-face, the positions of the 6 notches correspond to the hours: 1, 3, 5, 7, 9, 11.

With reference to FIGS. 1, 3, 4A and 4B, a movable portion 6 is provided, comprising a rotation segment 6a and an operating segment 6b, both of which are hollow and are made of a disposable plastic material. The two segments can be associated together through a female thread F (indicated by a broken line) comprised in the base of the operating segment 6b and housing a corresponding thread F' comprised in the rotation segment 6a. The rotation segment 6a is shapingly coupled with the support element 4 in such a way that it can be inserted inside the latter. Once the movable portion 6 has been assembled it can be inserted inside the support element 4 and rotate coaxially by 360° in relation to the latter. The rotation segment 6a is made in such a way as to enable the operating segment 6b to protrude outside the support element 4. The operating segment 6b is a hollow cylinder that is open at opposite ends and has a side wall 7 interrupted by an operating window 8. The latter is delimited by a U-shaped cut, the convex part of which reaches near the female thread F. The operating window 8 is made in such a way that the convex end of the U-shaped cut corresponds to the point that can be reached by the end of the index finger of the hand of a person of average build by inserting the index finger inside the anoscope. In this way the operating window 8 constitutes the area where the operator can enter in direct contact with the rectal mucous membrane to carry out the "Z" surgical sutures provided by the Sias method.

With reference to FIGS. 1, 3, 7 and 7A the movable portion 6 comprises a positioning element 9 that is integral with the rotation segment 6a and is positioned in such a way as to face the operator during use. The positioning element 9 is shaped in the form of a ring comprising a plurality of teeth 10, arranged to facilitate the operator's grip of said toothed element. The teeth 10 comprise a locking tooth 10' (shown enlarged in detail 7A), that is marked by a navigator 30 and comprises a recess 11 housing a peg 11'. Between the bottom of the recess 11 and the end of the peg 11' next to said bottom a coil spring 12 is placed by which the peg 11' protrudes outside the recess 11. When the anoscope 1 is assembled, as the positioning element 9 is juxtaposed on the edge 4'a comprised in the support element 4 and as the recess 11 is arranged in such a way that the protruding end of the peg 11' comes into contact with said edge, the peg 11' is forced to retract completely into the recess 11, thereby compressing the spring 12. By rotating the positioning element 9 by 360° in relation to the fixed portion 4, the locking tooth 10' subsequently comes into contact with each of the notches 5 comprised in the edge 4'a. At each notch 5, the peg 11' can emerge from the recess 11, assisted by the relaxation of the spring 12, and partially penetrates inside the notch 5. In this way the positioning element 9, and therefore the movable portion 6, can be locked in each of the 6 positions defined by the notches 5. By slightly forcing the positioning element 9 it can be released and further rotated until it reaches the next notch 5.

The 6 fixed positions that can be reached by the locking tooth 10' correspond to analogous positions of the operating window 8 in relation to the internal wall of the rectum. If for example, as illustrated in FIG. 8, the operator rotates the positioning element 9 until the locking tooth 10' fits in the notch 5 corresponding to 9 o'clock, the simultaneous rotation of the movable portion 6 also places the operating window 8 in the position corresponding to 9 o'clock. In this manner, the operator, by orienting the anoscope with the grip parallel to the intergluteal sulcus of a patient, can easily reach, through the rotating operating window, the zones of the rectal mucous membrane corresponding to those envisaged by the Sias method for surgically treating haemorrhoids.

With reference to FIG. 5, a prior-art dilator 20 is provided, said dilator being made of a material with a low attrition coefficient (e.g., Teflon) and which is shapingly coupled with the movable portion 6.

The operator uses the dilator 20 by positioning it inside the anoscope 1, when he inserts the latter through the anal region of a patient. The dilator 20 is shaped in such a way as to dilate the intestinal lumen to precede and facilitate the entry of the anoscope 1. Once the anoscope 1 has been located, the dilator 20 can be extracted, thus making the intestinal lumen accessible to the operator. Before the movable portion 6 is rotated, the dilator 20 is reinserted by the operator to relax the rectal mucous membrane and thereby facilitate said rotation.

The anoscope 1, in addition to being used for carrying out the Sias surgical method, can be effectively used for: making elastic ligatures, cryotherapy, removing intestinal polyps, administering sclerosing injections, and carrying out diagnoses and transanal therapy in general.

The invention claimed is:

1. An anoscope comprising a first hollow body open at opposite ends and a second hollow body open at opposite ends shapingly coupled with said first hollow body and arranged to coaxially rotate inside said first hollow body, said second hollow body being provided with a window arranged to make a portion of rectal mucous membrane accessible, wherein an angular positioning element is provided to adjust the relative angular position of said second hollow body in said first hollow body in preset reciprocal angular positions, said reciprocal angular positions corresponding to a same number of positions that can be taken up by said window, wherein the first and second hollow bodies are rotatable relative to one another while the operating window maintains a constant size and allows access to the rectal mucous membrane at all of said reciprocal angular positions, wherein said first hollow body comprises a first truncated-cone portion and has an edge that is comprised in a base of said first truncated-cone portion, said edge comprising a plurality of notches, wherein said second hollow body comprises a rotation segment and an operating segment that can be associated with one another before use, said angular positioning element being integral with said rotation segment, wherein said angular positioning element comprises a plurality of teeth, said plurality of teeth comprising a locking tooth that comprises a recess housing a peg, wherein the rotation of said angular positioning element can be locked by an interaction between said peg and each of said notches.

2. An anoscope according to claim 1, wherein said window has dimensions and a shape such as to enable a surgical device to intervene on said portion.

3. An anoscope according to claim 1, wherein said first truncated-cone portion is solidly connected with a second truncated-cone portion that has a progressively decreasing cross-section.

4. An anoscope according to claim 3, wherein said second truncated-cone portion is solidly connected with a third truncated-cone portion that protrudes from a part opposite said first truncated-cone portion and has a progressively decreasing cross-section.

5. An anoscope according to claim 1, wherein said window is arranged on said operating segment.

6. An anoscope according to claim 1, wherein said operating window is defined by a U-shaped cut.

7. An anoscope according to claim 1, wherein said window opens near to the point that can be reached by the tip of an index finger of a hand of an individual of medium build, by inserting said index finger inside said second hollow body.

8. An anoscope according to claim 1, wherein said notches are 6 in number.

9. An anoscope according to claim 8, wherein said notches are arranged along said edge according to the hours on an imaginary clock-face.

10. An anoscope according to claim 9, wherein said notches are arranged at 1 o'clock, 3 o'clock, 5 o'clock, 7 o'clock, 9 o'clock, 11 o'clock.

11. An anoscope according to claim 1, comprising an elastic element interposed between said peg and the bottom of said recess.

12. An anoscope according to claim 1, wherein the operating window is positioned beyond the distal end of the first hollow body.

13. An anoscope according to claim 1, wherein the preset angular positions correspond to arterial branches of a patient's rectal wall.

14. An anoscope according to claim 6, wherein a convex portion of the U-shaped operating window is oriented towards the first hollow body, and an open end of the U-shaped operating window is arranged at a distal end of the second hollow body.

15. An anoscope according to claim 1, wherein the window of the second hollow body is provided at a distal end of the second hollow body, and the second hollow body protrudes outside and beyond a distal end of the first hollow body.

16. An anoscope according to claim 1, wherein the positioning element includes a locking member that maintains alignment with the window during rotation of the second hollow body.

* * * * *